United States Patent [19]

Wehling

[11] 4,289,887
[45] Sep. 15, 1981

[54] BENZOFURANE BENZOXAZOLES

[75] Inventor: Bernhard Wehling, Cologne, Fed. Rep. of Germany

[73] Assignee: Bayer Aktiengesellschaft, Leverkusen, Fed. Rep. of Germany

[21] Appl. No.: 141,831

[22] Filed: Apr. 21, 1980

[30] Foreign Application Priority Data

May 11, 1979 [DE] Fed. Rep. of Germany ....... 2918965

[51] Int. Cl.³ ..................... C07D 263/58; C09K 11/06
[52] U.S. Cl. ............................. 548/224; 252/301.24
[58] Field of Search ......................................... 548/224

[56] References Cited

U.S. PATENT DOCUMENTS 3,974,172  8/1976  Sahm et al. ......................... 548/224
4,016,172  4/1977  Harnisch ............................. 548/224

FOREIGN PATENT DOCUMENTS 2162439  6/1973  Fed. Rep. of Germany .

Primary Examiner—Anton H. Sutto
Attorney, Agent, or Firm—Sprung, Felfe, Horn, Lynch & Kramer

[57] ABSTRACT

Compounds of the formula

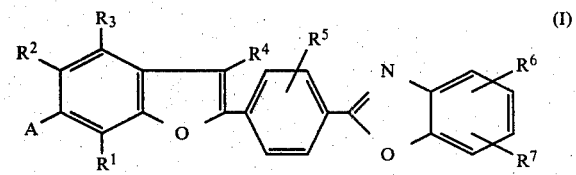

in which
R¹, R² and R³ denote hydrogen, alkyl, alkoxy or halogen,
A denotes aryl or a radical of the formula

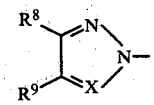

wherein
R⁸ denotes aryl, alkyl, aralkyl, styryl or alkoxy,
R⁹ denotes hydrogen, CN, COOR, CONRR' or R⁸ and X denotes N or C(R¹⁰),
R⁴ and R¹⁰ denote hydrogen, alkyl or aryl,
R⁵, R⁶ and R⁷ denote hydrogen, halogen or alkyl, inter alia,
R denotes alkyl and
R' denotes R or H,
are valuable optical brighteners for polyesters, polyamides, cellulose esters and polyacrylonitrile.

2 Claims, No Drawings

BENZOFURANE BENZOXAZOLES

The invention relates to compounds of the formula

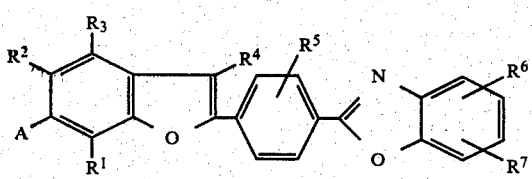

in which
 $R^1$, $R^2$ and $R^3$ denote hydrogen, alkyl, alkoxy or halogen,
 A denotes aryl or a substituent of the general formula

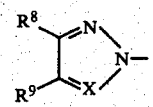

in which
 $R^8$ denotes aryl, alkyl, aralkyl, styryl or alkoxy, and
 $R^9$ denotes hydrogen, CN, COOR, CONRR' or $R^8$, or
 $R^8$ and $R^9$ together denote a fused-on hydroaromatic or aromatic ring, and
 X denotes N or $C(R^{10})$,
 $R^{10}$ denotes hydrogen, alkyl or aryl,
 $R^4$ denotes hydrogen, aryl or alkyl,
 $R^5$ denotes hydrogen, halogen or alkyl,
 $R^6$ denotes hydrogen, halogen, alkyl, alkoxy, alkylsulphonyl, phenylsulphonyl, CN, $CF_3$, COOR, $SO_3R$, CONRR' or $SO_2NRR'$,
 $R^7$ denotes hydrogen, halogen, alkyl or alkoxy, R denotes alkyl and
 R' denotes R or H,
and wherein the abovementioned hydrocarbon radicals and alkoxy radicals and the optionally fused-on ring systems can be substituted by substituents customary in brightener chemistry.

Suitable alkyl and alkoxy radicals in any context have 1 to 4 C atoms, and methyl, ethyl, methoxy and ethoxy are preferred.

Suitable aryl radicals are phenyl radicals which are optionally substituted by alkyl, alkoxy, halogen, CN, COOR and $SO_2R$, inter alia. "Halogen" is understood, above all, as bromine and, in particular, chlorine.

Suitable aralkyl radicals are phenylalkyl radicals which are optionally substituted by alkyl, alkoxy, halogen, CN, COOR and $SO_2R$, inter alia.

Suitable fused-on rings are optionally substituted cyclohexane, benzene or naphthalene rings.

Compounds of the formula (I) wherein
 $R^1$, $R^2$ and $R^3$ denote hydrogen, methyl, ethyl, methoxy or chlorine,
 A denotes phenyl which is substituted by $C_1$–$C_4$-alkyl and/or $C_1$–$C_4$-alkoxy, or a substituent of the general formula

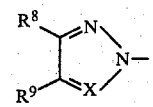

in which
 $R^8$ denotes $C_1$–$C_4$-alkyl, $C_1$–$C_4$-alkoxy, a phenyl radical which is optionally substituted by $C_1$–$C_4$-alkyl, phenyl, $C_1$–$C_4$-alkoxy or chlorine, benzyl or styryl and
 $R^9$ denotes hydrogen, cyano, carboxyl, $C_1$–$C_4$-alkylcarbonylamino, benzoylamino or $R^8$, or
 $R^8$ and $R^9$ together denote a fused-on naphthalene or benzene ring, which can optionally be substituted by $C_1$–$C_4$-alkyl and/or $C_1$–$C_4$-alkoxy, and X denotes N or $C(R^{10})$,
 $R^{10}$ denotes hydrogen, $C_1$–$C_4$-alkyl or phenyl,
 $R^4$ denotes hydrogen, alkyl with 1 to 4 C atoms, preferably methyl, or phenyl which is optionally substituted by methyl and/or methoxy,
 $R^5$ denotes hydrogen, chlorine or $C_1$–$C_4$-alkyl,
 $R^6$ denotes hydrogen, alkyl with 1 to 4 C atoms, preferably methyl, methoxy, chlorine, alkylsulphonyl with 1 to 4 C atoms, cyano, COOH, $SO_3H$, $COOR^{11}$, $SO_3R^{11}$ or $CON(R^4)_2$,
 $R^7$ denotes hydrogen, $C_1$–$C_4$-alkyl, methoxy or chlorine and
 $R^{11}$ denotes $C_1$–$C_4$-alkyl, preferably methyl, $C_2$–$C_4$-hydroxyalkyl, cyanoethyl, phenyl which is optionally substituted by chlorine, methyl or methoxy, cyclohexyl or benzyl,
are of particular importance from an industrial point of view.

The compounds of the formula (I) can be prepared by various methods. One variant is characterised in that compounds of the formula

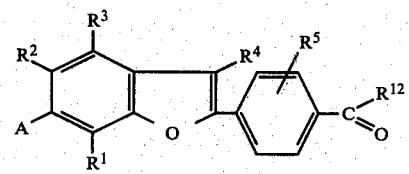

in which
 $R^{12}$ denotes alkoxy, chlorine or bromine, are reacted with compounds of the formula

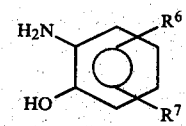

in a manner which is known per se (compare DE-OS (German Published Specification) 2,162,439).

The compounds of the formula (I) can furthermore be prepared by a process in which compounds of the formula

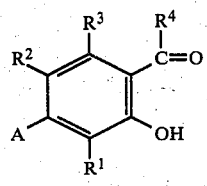 (IV)

or salts thereof, are first reacted with compounds of the formula

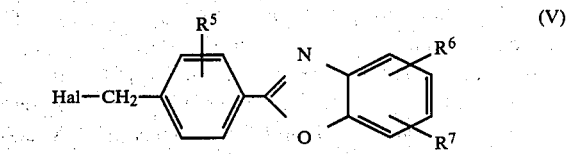 (V)

in which
Hal denotes chlorine or bromine,
to give products of the formula

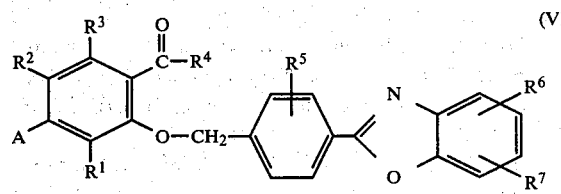 (VI)

and these are then cyclised to give compounds of the formula (I).

Compounds of the formula (I) can also be prepared by reacting a compound of the formula

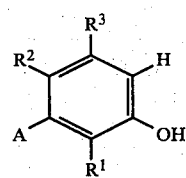 (VII)

with a compound of the formula

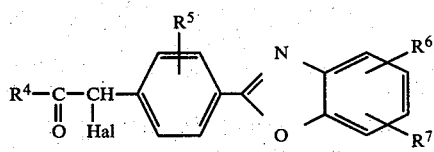 (VIII)

Compounds of the formula (I) in which $R^4$ denotes H can also be formed by condensation of compounds of the formula (VII) with compounds of the formula

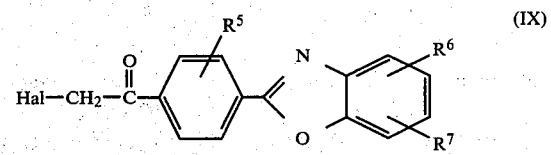 (IX)

to give the intermediate products of the formula

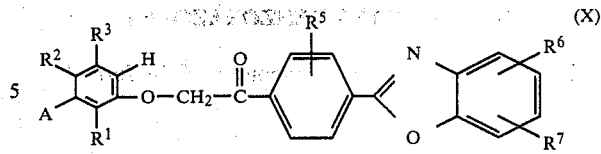 (X)

and subsequent rearrangement of these compounds.

The new compounds are suitable as optical brighteners for natural and synthetic fibres, in particular polyesters, polyamides, cellulose esters and polyacrylonitrile. They are also suitable for bulk brightening of these substrates.

EXAMPLE 1

5.9 g of 2-aminophenol are dissolved in 120 ml of pyridine, and 20 g of 2-(4-chlorocarbonyl-phenyl)-6-(4-methyl-5-phenyl-1,2,3-triazol-2-yl)-benzofurane are added in small portions in the course of 15 minutes. The reaction mixture is warmed to 80° C. for 8 hours. It is then cooled to room temperature and poured onto 1,000 ml of 10% strength hydrochloric acid and the solid is filtered off, washed until the runnings are neutral and dried. The intermediate product of the formula

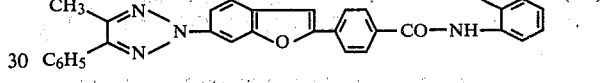 (101)

is heated in a mixture of 140 ml of trichlorobenzene and 0.2 g of boric acid to 200° C. for 4 hours and the water formed is distilled off. The mixture is then stirred until cold and the solid is filtered off, washed with methanol and dried at 100° C. After recrystallisation from glycol monomethyl ether/active charcoal, 13.5 g (60% of theory) of the compound of the formula

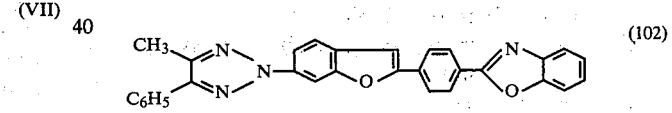 (102)

which exhibits blue fluorescence when dissolved in dimethylformamide, are obtained.

2-(4-Chlorocarbonyl-phenyl)-6-(4-methyl-5-phenyl-1,2,3-triazol-2-yl)-benzofurane is prepared as follows:

100 g of 4-(4-methyl-5-phenyl-1,2,3-triazol-2-yl)-salicylaldehyde, 47 g of 4-cyanobenzyl chloride and 62.2 g of potassium carbonate are heated in 700 ml of dimethylsulphoxide to 80° C. for 8 hours. The reaction mixture is then poured onto 3,000 ml of water and rendered acid to Congo Red with concentrated hydrochloric acid and the solid is filtered off and washed until the runnings are neutral. The still moist intermediate product is dissolved in 1,300 ml of dimethylformamide at 80° C., 76 g of potassium hydroxide powder (88% pure) are added at 30° C. and the mixture is stirred at 30° C. for 5 hours. It is poured onto 5,000 ml of water and rendered acid to Congo Red with concentrated HCl and the solid is filtered off, washed until the runnings are neutral and dried at 100° C. The crude product is refluxed in 1,200 ml of glycol monomethyl ether and 730 ml of 50% strength potassium hydroxide solution for 13 hours. The reaction mixture is poured onto a mixture of 970 ml of concentrated hydrochloric acid and 1,940 g of ice and the precipitate is filtered off, washed until the runnings are neutral and dried at 100° C. Yield: 95 g (80.2% of theory) of 2-(4-carboxy-phenyl)-6-(4-methyl-5-phenyl-1,2,3-triazol-2-yl)-benzofurane of melting point 275° C. The carboxylic acid is stirred in 940 ml of distilled toluene, 117.5 g of thionyl chloride and 5 ml of dimethylformamide are added and the mixture is heated gradually to the boiling point. It is refluxed for 1 hour and clarified with active charcoal, the filtrate is cooled and the solid is filtered off and dried in vacuo at 80° C.

Yield: 71.6 g (72% of theory) of 2-(4-chlorocarbonyl-phenyl)-6-(4-methyl-5-phenyl-1,2,3-triazol-2-yl)-benzofurane of melting point 201° C.

EXAMPLE 2

The compound of the formula (101) can also be prepared in the following manner:

9.2 g of the sodium salt of 4-(4-methyl-5-phenyl-1,2,3-triazol-2-yl)-salicylaldehyde (98.2% pure) and 7.3 g of 2-(4-chloromethyl-phenyl)-benzoxazole are stirred in 250 ml of dimethylformamide at 70° C. for 8 hours. 14.2 g of potassium tert.-butylate (95% pure) are then added at room temperature and the mixture is stirred at 60° C. for 4 hours. After pouring the mixture onto 500 ml of water, the solid is filtered off, washed until the runnings are neutral and dried at 100° C. When recrystallised from glycol monomethyl ether/active charcoal, 12.2 g (86.9% of theory) of a compound which is identical to the compound of the formula (101) and exhibits blue fluorescence in solution in dimethylformamide are obtained.

EXAMPLE 3

If the 2-(4-chloromethyl-phenyl)-benzoxazole is replaced by the correspondingly substituted analogues and the procedure is otherwise as described in Example 2, the following compounds of the formula

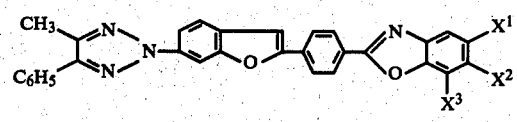

are obtained.

| No. | X¹ | X² | X³ | Colour of fluorescence in solution in dimethylformamide |
|---|---|---|---|---|
| 301 | CH₃ | H | H | blue |
| 302 | CH₃ | H | CH₃ | blue |
| 303 | CH₃ | CH₃ | H | blue |
| 304 | C(CH₃)₃ | H | H | blue |
| 305 | Cl | H | H | blue-green |
| 306 | CO₂CH₃ | H | H | blue-green |

EXAMPLE 4

If the sodium salt of 4-(4-methyl-5-phenyl-1,2,3-triazol-2-yl)-salicylaldehyde is replaced by the sodium salt of 4-(4-ethyl-5-methyl-1,2,3-triazol-2-yl)-salicylaldehyde, the compounds of the formula

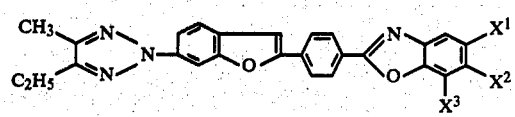

are obtained analogously to Example 2:

| No. | X¹ | X² | X³ | Colour of fluorescence in solution in dimethylformamide |
|---|---|---|---|---|
| 401 | H | H | H | blue-violet |
| 402 | CH₃ | H | H | blue |
| 403 | CH₃ | H | CH₃ | blue |
| 404 | CH₃ | CH₃ | H | blue |
| 405 | C(CH₃)₃ | H | H | blue |
| 406 | Cl | H | H | blue-green |
| 407 | CO₂CH₃ | H | H | blue-green |

EXAMPLE 5

Using the sodium salt of 4-(naphth[1,2-d]-1,2,3-triazol-2-yl)-salicylaldehyde, the compounds of the formula

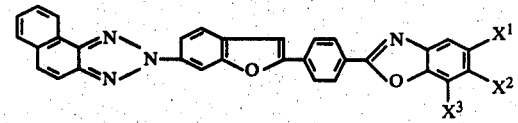

are obtained analogously to Example 2:

| No. | X¹ | X² | X³ | Colour of fluorescence in solution in dimethylformamide |
|---|---|---|---|---|
| 501 | H | H | H | blue |
| 502 | CH₃ | H | H | blue-green |
| 503 | CH₃ | H | CH₃ | blue-green |
| 504 | CH₃ | CH₃ | H | blue-green |
| 505 | C(CH₃)₃ | H | H | blue-green |
| 506 | Cl | H | H | blue-green |
| 507 | CO₂CH₃ | H | H | blue-green |

EXAMPLE 6

Using the sodium salt of 4-phenyl-salicylaldehyde or of 2-hydroxy-4-phenyl-acetophenone, the compounds of the formula

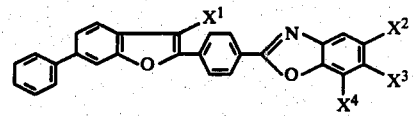

are obtained analogously to Example 2:

| No. | X¹ | X² | X³ | X⁴ | Colour of fluorescence in solution in dimethylformamide |
|---|---|---|---|---|---|
| 601 | H | H | H | H | violet |
| 602 | H | CH₃ | H | H | blue-violet |
| 603 | H | CH₃ | H | CH₃ | blue |
| 604 | H | CH₃ | CH₃ | H | blue |
| 605 | H | C(CH₃)₃ | H | H | blue-violet |
| 606 | H | Cl | H | H | blue |
| 607 | H | CO₂CH₃ | H | H | blue-green |
| 608 | CH₃ | H | H | H | violet |
| 609 | CH₃ | CH₃ | H | H | blue-violet |
| 610 | CH₃ | CH₃ | H | CH₃ | blue |
| 611 | CH₃ | CH₃ | CH₃ | H | blue |
| 612 | CH₃ | C(CH₃)₃ | H | H | blue-violet |
| 613 | CH₃ | Cl | H | H | blue-violet |
| 614 | CH₃ | CO₂CH₃ | H | H | blue |

I claim:
1. A benzofurane compound of the formula

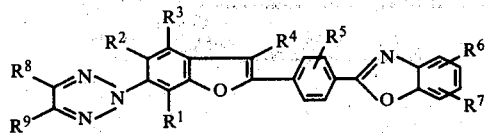

in which
- $R^1$, $R^2$ and $R^3$ denote hydrogen, alkyl, alkoxy or halogen,
- $R^4$ denotes hydrogen, aryl or alkyl,
- $R^5$ denotes hydrogen, halogen, or alkyl,
- $R^6$ denotes hydrogen, halogen, alkyl, alkoxy, alkylsulphonyl, phenylsulphonyl, CN, $CF_3$, COOR, $SO_3R$, CONRR' or $SO_2NRR'$,
- $R^7$ denotes hydrogen, halogen, alkyl or alkoxy,
- R denotes alkyl and
- R' denotes alkyl or H,
- $R^8$ denotes aryl, alkyl, aralkyl, styryl or alkoxy, and
- $R^9$ denotes hydrogen, CN, COOR, CONRR' or $R^8$, or $R^8$ and $R^9$ together denote a fused-on hydroaromatic or aromatic ring, and the abovementioned hydrocarbon radicals and alkoxy radicals and the optionally fused-on ring systems optionally being substituted by substituents customary in brightener chemistry.

2. A benzofurane compound according to claim 1, of the formula

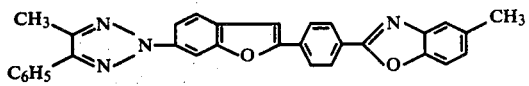

* * * * *